US008765638B2

(12) United States Patent
Hacker et al.

(10) Patent No.: US 8,765,638 B2
(45) Date of Patent: *Jul. 1, 2014

(54) HERBICIDAL COMPOSITIONS

(71) Applicant: Bayer Intellectual Property GmbH, Monheim (DE)

(72) Inventors: Erwin Hacker, Hochheim (DE); Hermann Bieringer, Eppstein (DE); Thomas Auler, Kelsterbach (DE); Alvaro Melendez, Schwalbach (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/722,630

(22) Filed: Dec. 20, 2012

(65) Prior Publication Data

US 2013/0143743 A1  Jun. 6, 2013

Related U.S. Application Data

(63) Continuation of application No. 10/241,972, filed on Sep. 12, 2002, now Pat. No. 8,357,629, which is a continuation of application No. 09/353,230, filed on Jul. 14, 1999, now abandoned.

(30) Foreign Application Priority Data

Jul. 16, 1998 (DE) ................................. 198 32 017
Jun. 22, 1999 (DE) ................................. 199 28 387

(51) Int. Cl.
| | | |
|---|---|---|
| A01N 43/36 | (2006.01) | |
| A01N 47/12 | (2006.01) | |
| A01N 47/36 | (2006.01) | |
| A01N 37/22 | (2006.01) | |
| A01N 43/76 | (2006.01) | |
| A01N 43/82 | (2006.01) | |
| A01N 41/02 | (2006.01) | |
| A01N 43/12 | (2006.01) | |
| A01N 43/40 | (2006.01) | |
| A01N 43/653 | (2006.01) | |
| A01N 43/713 | (2006.01) | |
| A01N 43/86 | (2006.01) | |
| A01N 43/54 | (2006.01) | |

(52) U.S. Cl.
CPC ............. *A01N 43/76* (2013.01); *A01N 47/12* (2013.01); *A01N 47/36* (2013.01); *A01N 37/22* (2013.01); *A01N 43/82* (2013.01); *A01N 41/02* (2013.01); *A01N 43/12* (2013.01); *A01N 43/40* (2013.01); *A01N 43/653* (2013.01); *A01N 43/713* (2013.01); *A01N 43/86* (2013.01); *A01N 43/54* (2013.01)
USPC ........................................................ 504/138

(58) Field of Classification Search
CPC ............................... A01N 43/76; A01N 37/22
See application file for complete search history.

(56) References Cited

U.S. PATENT DOCUMENTS

| | | | |
|---|---|---|---|
| 4,645,526 A | 2/1987 | Bauer et al. | |
| 4,668,276 A | 5/1987 | Handte et al. | |
| 4,904,295 A | 2/1990 | Mayland et al. | |
| 5,080,709 A | 1/1992 | Schumacher et al. | |
| 5,447,903 A | 9/1995 | Ort et al. | |
| 5,502,271 A | 3/1996 | Donn et al. | |
| 5,532,209 A * | 7/1996 | Houghton et al. | 504/339 |
| 5,629,262 A | 5/1997 | Auxier et al. | |
| 5,705,456 A | 1/1998 | Mitchell et al. | |
| 5,935,905 A | 8/1999 | Mito et al. | |
| 5,945,379 A * | 8/1999 | Dollinger et al. | 504/130 |
| 8,357,629 B2 * | 1/2013 | Hacker et al. | 504/100 |

FOREIGN PATENT DOCUMENTS

| | | |
|---|---|---|
| CA | 1168884 | 6/1984 |
| CA | 2230113 | 3/1998 |
| CA | 2230120 | 3/1998 |
| DE | 4336953 | 8/1994 |
| DE | 4428982 | 5/1996 |
| DE | 19534910 | 3/1997 |
| DE | 19834627 | 12/1998 |
| DE | 19851854 | 4/1999 |
| EP | 0043802 | 1/1982 |
| EP | 0293062 | 11/1988 |
| EP | 0614608 | 9/1994 |
| GB | 2137092 | 3/1984 |
| WO | WO/94/09629 | 5/1994 |
| WO | WO/97/10710 | 3/1997 |
| WO | WO/9854967 | 12/1998 |

OTHER PUBLICATIONS

The Agrochemicals Handbook, 3rd Edition, Royal Society of Chemistry, p. A1267/Aug. 91).*
Patent Abstracts of Japan, vol. 4, No. 61 (1980), JP 55.
English language abstract of EP0482491 published Apr. 29, 1992.
The Agrochemicals Handbook, 3rd Edition, Royal Society of Chemistry, p. A 1267, Aug. 1991.
Bhowmik, Fenoxaprop-ethyl for Postemergence Crabgrass Control in Kentucky Bluegrass Turf, HortScience, 1986, 21(3), pp. 457-458.
European Search Report forPCT/EP99/04788 dated Apr. 14, 2000.

* cited by examiner

*Primary Examiner* — Alton Pryor
(74) *Attorney, Agent, or Firm* — Frommer Lawrence & Haug LLP

(57) ABSTRACT

A herbicide combination comprising of components (A) and (B) exhibit synergistic herbicidal effects, where
(A) is one or more herbicides selected from the group consisting of heteroaryloxy- and aryloxy-phenoxypropionic acids, their salts and esters and cyclohexanediones, and
(B) is one or more herbicides selected from the group consisting of
(B1) herbicides which are selective in rice, mainly against mono-cotyledonous plants,
(B2) herbicides which are selective in rice, mainly against dicotyledonous harmful plants and cyperaceae,
(B3) herbicides which are selective in rice, mainly against cyperaceae and
(B4) herbicides which are selective in rice, mainly against mono-cotyledonous and dicotyledonous plants and cyperaceae.

3 Claims, No Drawings

HERBICIDAL COMPOSITIONS

The present application is a continuation of U.S. patent application Ser. No. 10/241,972 filed on Sep. 12, 2002, which is a continuation of U.S. patent application Ser. No. 09/353,230 filed on Jul. 14, 1999, which claims priority from German Patent Application Nos. DE 199 28 387.7 and DE 198 32 017.5 filed on Jun. 22, 1999 and Jul. 16, 1998 respectively, the disclosures of which are incorporated herein by reference in their entirety.

The invention is in the field of crop protection compositions which can be used against harmful plants in crops, preferably in rice, and which comprise, as herbicidally active compounds, a combination of at least two herbicides, one herbicide component being selected from the group consisting of the herbicides of the type of the fatty acid biosynthesis inhibitors.

A number of compounds from the structure class of the aryloxyphenoxypropionic acids, cyclohexanediones and derivatives of the abovementioned compounds and their derivatives are known as herbicides of the type of the fatty acid biosynthesis inhibitors. An advantage of these compounds is their activity against grasses, and a selective use, if appropriate in combination with safeners, is possible and utilized even in monocotyledonous crops.

The effectiveness of these herbicides against harmful plants in the crops is at a high level; however, it depends in general on the application rate, the respective formulation, the harmful plants to be controlled in each case or the spectrum of harmful plants, the climatic and soil conditions, etc. A further criterion is the duration of the action, or the rate of degradation of the herbicide. Also to be taken into account are, if appropriate, changes in the susceptibility of harmful plants toward an active compound which may occur on prolonged use or in geographical locations. Activity losses in individual plants can only be compensated to a certain extent by higher application rates of the herbicides, for example because this frequently decreases the selectivity of the herbicides, or an improvement in activity is not observed, even at higher application rates. In some cases, it is possible to improve the selectivity in crops by addition of safeners. In general, however, there is always a need for methods to achieve the herbicidal action with a lower application rate of active compounds. A lower application rate reduces not only the amount of an active compound which is required for the application, but generally also reduces the amount of formulation auxiliaries required. Both reduce the economic expense and improve the ecological compatibility of the herbicide treatment. A method for improving the property profile of a herbicide may consist in the combination of the active compound with one or more other active compounds which contribute the desired additional properties. However, when two or more active compounds are applied in combination, it is not uncommon for phenomena of physical and biological incompatibility to occur, for example lack of stability of a coformulation, decomposition of an active compound or antagonism of the active compounds. In contrast, what is desired are combinations of active compounds having a favorable activity profile, high stability and as synergistically enhanced an activity as possible which permits a reduction of the application rate, compared with the individual application of the active compounds to be combined.

Surprisingly, it has now been found that active compounds from the abovementioned herbicide classes interact in a particularly favorable manner in combination with certain structurally different herbicides when they are used against harmful plants in crops of rice. The use applies preferably to crops of rice which are substantially tolerant to the use of the herbicides, if appropriate with addition of safeners. By introducing tolerant or resistant varieties or lines of rice, in particular transgenic varieties and lines of rice, the customary system of weed control is supplemented by new active compounds which, per se, are nonselective in customary varieties of rice.

The combinations according to the invention are furthermore frequently also suitable for controlling the same harmful plants in other crops.

The invention accordingly provides herbicide combinations having an effective content of components (A) and (B), where (A) is one or more herbicides selected from the group consisting of heteroaryloxy- and aryloxy-phenoxypropionic acids, their salts and esters and cyclohexanediones, and (B) is one or more herbicides which are structurally different from the herbicides (A) contained in each case, selected from the group of the compounds consisting of (B1) herbicides which are selective in rice, mainly against monocotyledonous plants, (B2) herbicides which are selective in rice, mainly against dicotyledonous harmful plants and cyperaceae, (B3) herbicides which are selective in rice, mainly against cyperaceae and (B4) herbicides which are selective in rice, mainly against monocotyledonous and dicotyledonous harmful plants and cyperaceae.

The herbicide combinations according to the invention may contain other components, for example other herbicides, insecticides, fungicides, acaricides, crop protection agents of a different type (for example safeners), plant growth regulators and/or additives and/or formulation auxiliaries which are customary in crop protection. Here, the components can be formulated jointly (ready-to-use formulation) and used, or they can be formulated separately and used jointly, for example in the tank mix or in sequential application.

The synergistic effects are observed when the active compounds (A) and (B) are applied jointly; however, they can also frequently be observed when the active compounds are applied at different times (splitting). It is also possible to apply the herbicides or the herbicide combinations in a plurality of portions (sequential application), for example after pre-emergence applications, followed by post-emergence applications or after early post-emergence applications, followed by medium or late post-emergence applications. Preference is given here to the joint or almost simultaneous application of the active compounds of the combination in question, if appropriate in a plurality of portions. However, it is also possible to apply the individual active compounds of a combination at different times, which may be advantageous in the individual case. It is also possible to integrate other crop protection agents, such as fungicides, insecticides, acaricides, etc., and/or various auxiliaries, adjuvants and/or fertilizer applications, into this system application.

By the combined use of the herbicides (A) and (B), it is possible to achieve use properties which exceed what was to be expected based on the known properties of the individual herbicides for their combination. The synergistic effects permit a reduction of the application rates of the individual active compounds, a higher efficacy at the same application rate, the control of harmful plants which were as yet uncontrolled (gaps), an extension of the period of application and/or a reduction in the number of individual applications required and—as a result for the user—weed control systems which are more advantageous economically and ecologically.

Suitable combination partners (A) are, for example, the compounds (A1) and (A2) below, which can in each case be employed on their own or in combination with one another (in most cases, the herbicides are referred to by the common name for the active compound, in accordance with the reference "The Pesticide Manual" 11th Ed., British Crop Protection Council 1997, abbreviated "PM"):

(A1) herbicides from the group of the (hetero)aryloxyphenoxypropionic acids and their derivatives, which are active against monocotyledonous harmful plants, mainly via the leaf, and which can be used selectively in rice, if appropriate in combination with suitable safeners, for example (A1.1) "fenoxaprop-P" and its esters, such as the ethyl ester "fenoxaprop-P-ethyl" (see PM, pp. 519-520) (=(R)-2-[4-(6-chlorobenzoxyzolyl-2-yloxy)phenoxy]propionic acid or its ethyl ester), also in the use form of the racemate "fenoxaprop" and its esters, such as the ethyl ester, and/or (A1.2) "quizalofop-P" and its esters, such as the ethyl or tefuryl ester (see PM, pp. 1089-1092) (=(R)-2-[4-(6-chloroquinoxalin-2-yloxy)phenoxy]propionic acid or its ethyl ester or tetrahydrofurfuryl ester), also in the form of the racemate "quizalofop" and its esters; cf. also, as specific ester, "propaquizafop" (compound A1.3), and/or (A1.3) "propaquizafop" (PM, pp. 1021-1022), the 2-isopropylideneaminooxyethyl ester of quizalofop-P and/or (A1.4) "fluazifop-P" and its esters, such as the butyl ester (see PM, pp. 556-557) (=(R)-2-[4-(5-trifluoromethylpyrid-2-yloxy)phenoxy]propionic acid or its butyl ester), also in the use form of the racemate "fluazifop" and its esters, and/or (A1.5) "haloxyfop-P" and its esters, such as the methyl ester (see PM, pp. 660-663) (=(R)-2-[4-(3-chloro-5-trifluoromethylpyrid-2-yloxy)phenoxy]propionic acid or its methyl ester), also in the use form of the racemate "haloxyfop" and its esters, such as the methyl or the etotyl ester and/or (A1.6) "cyhalofop" and its esters, such as the butyl ester (PM, pp. 297-298) (=(R)-2-[4-(4-cyano-2-fluorophenoxy)phenoxy]propionic acid or its butyl ester) and/or (A1.7) "clodinafop" and its esters, such as the propargyl ester (PM, pp. 251-252) (=(R)-2-[4-(5-chloro-3-fluoropyrid-2-yloxy)phenoxy]propionic acid or its propargyl ester).

(A2) Herbicides of the group of the cyclohexanediones which are active against monocotyledonous harmful plants via the leaf and the soil and which can be employed selectively in rice, for example (A2.1) "sethoxydim" (PM, pp. 1101-1103) (=(RS)-(EZ)-2-(1-ethoxyiminobutyl)-5-[5-(ethylthio)propyl]-3-hydroxycyclohexen-2-enone) and/or (A2.2) "cycloxydim" (PM, pp. 290-291) (=(RS)-2-(1-ethoxyiminobutyl)-5-[5-(ethylthio)propyl]-3-hydroxy-5-thian-3-ylcyclohexen-2-enone) and/or (A2.3) "clethodim" (PM, pp. 250-251) (=(RS)-2-{(E)-1-[(E)-3-chloroallyloxyimino]propyl}-5-[2-(ethylthio)propyl]-3-hydroxycyclohexen-2-enone).

(A2.4) "clefoxidim" or "BAS 625 H" (see AG Chem New Compound Review, Vol. 17, 1999, p. 26, published by AGRANOVA) (=2-[1-2-(4-chlorophenoxy)propoxyimino)butyl]-3-oxo-5-thion-3-ylcyclohex-1-enol).

The application rates of the herbicides (A) are known in principle and are, for the herbicides of type (A1), in the range from 5 g to 500 g of active substance per hectare and, for the herbicides of type (A2), in the range from 10 g to 1000 g of active substance per hectare. In the context of the abovementioned application rates, the mixtures according to the invention require lower application rates of the particular active compound, compared to the individual application.

Suitable combination partners (B) are, for example, the following compounds of the subgroups (B1) to (B4) which are different from the compounds (A) (the herbicides are in most cases referred to by the common name, in accordance with the reference "The Pesticide Manual" 11th Ed., British Crop Protection Council 1997, abbreviated "PM"):

(B1) Herbicides which are selective in rice, in particular against monocotyledonous harmful plants, are, for example, one or more compounds selected from the group consisting of (B1.1) butachlor (PM, pp. 159-160 (=N-(butoxymethyl)-2-chloro-N-(2,6-diethylphenyl)acetamide, (B1.2) butenachlor (PM, p. 1291) (=N-(but-2-enyloxymethyl)-2-chloro-N-(2,6-diethylphenyl)acetamide, (B1.3) thenylchlor (PM, pp. 1182-1183) (=2-chloro-N-(2,6-dimethylphenyl)-N-[(3-methoxy-2-thienyl)methyl]acetamide), (B1.4) pretilachlor (PM, pp. 995-996) (=2-chloro-N-(2,6-diethylphenyl)-N-(propoxyethyl)acetamide, (B1.5) mefenacet (PM, pp. 779-781) (=2-(1,3-benzthiazol-2-yloxy)-N-methylacetanilide, (B1.6) naproanilide (PM, pp. 865-866) (=N-phenyl-2-(2-naphthyloxy)-propionamide, (B1.7) propanil (PM, pp. 1017-1019) (=N-(3,4-dichlorophenyl)propanamide), (B1.8) etobenzanide (PM, pp. 492-493) (=N-(2,3-dichlorophenyl)-4-(ethoxyphenoxy)benzamide, (B1.9) dimepiperate (PM, pp. 404-405) (=S-1-methyl-1-phenylethyl piperidin-1-thiocarboxylate), (B1.10) molinate (PM, pp. 847-849) (=S-ethyl azepan-1-thiocarboxylate), (B1.11) thiobencarb (benthiocarb) (PM, pp. 1192-1193) (=S-4-chlorobenzyl diethyl thiocarbamate), (B1.12) pyributicarb (PM, pp. 1060-1061) (=O-3-tert-butylphenyl 6-methoxy-2-pyridyl(methyl)thiocarbamate, (B1.13) quinclorac (PM, pp. 1079-1080) (=3,7-dichloroquinoline-8-carboxylic acid), (B1.14) sulcotrione (PM, pp. 1124-1125), i.e. 2-(2-chloro-4-mesyl-benzoyl)cyclohexane-1,3-dione, (B1.15) fentrazamid (BAY NBA 061) (=N-cyclohexyl-N-ethyl-4-(2-chlorophenyl)-5-oxo-4,5-dihydrotetrazole-1-carboxamide), (B1.16) piperophos (PM, pp. 983-984) (=S-2-methyl-1-piperidinylcarbonylmethyl O,O-dipropyl dithiophosphate), (B1.17) JC-940 ("cumyluron") (=3-(2-chlorophenylmethyl)-1-(1-methyl-1-phenylethyl)urea, see JP-A-60087254), (B1.18) dithiopyr (PM, pp. 442-443) (=S,S'-dimethyl 2-difluoromethyl-4-isobutyl-6-trifluoromethylpyridin-3,5-di (thiocarboxylate), (B1.19) bromobutide (PM, pp. 144-145) (=2-bromo-3,3-dimethyl-N-(1-methyl-1-phenylethyl)butyramide), (B1.20) cinmethylin (PM, pp. 246-248) (=[(1RS,2SR,4SR)-1,4-epoxy-p-menth-2-yl) (2-methylbenzyl)ether) and (B1.21) cafenstrole (CH 900) (PM, pp. 173-174) (=N,N-diethyl-3-mesitylsulfonyl-1H-1,2,4-triazol-1-carboxamide), where in the case of the active compound (A1.2), (A1.3), (A1.4), (A1.5), (A2.1), (A2.2) or (A2.3), it is also possible to use (B1.22) anilofos (PM, pp. 47-48) (=S-4-chloro-N-isopropylcarbaniloylmethyl O,O-dimethyl dithiophosphate), as herbicidally active combination compound of the group (B1), alone or in combination with the abovementioned active compounds, and where in the case of the active compound (A1.1), it is also possible to use (B1.24) cyhalofop, in particular its butyl ester, and (B1.25) clodinafop and esters, in particular its propargyl ester,
as herbicidally active combination compound of the group (B1), alone or in combination with the abovementioned active compounds, and
where in the case of the active compound (A1.2) or (A1.3), it is also possible to use
(B1.24) cyhalofop and esters, in particular its butyl ester,
(B1.25) clodinafop and esters, in particular its propargyl ester,
(B1.26) fluazifop-(P) and its esters, in particular fluazifop-P-butyl,
(B1.27) haloxyfop-(P) and its esters, in particular haloxyfop-(P)-methyl,
(B1.28) sethoxydim,
(B1.29) cycloxydim,
(B1.30) clethodim and
(B1.31) clefoxidim
as herbicidally active combination compound of the group (B1), alone or in combination with the abovementioned active compounds, and
where in the case of the active compound (A1.4) or (A1.5), it is also possible to use
(B1.24) cyhalofop and esters, in particular its butyl ester,
(B1.25) clodinafop and esters, in particular its propargyl ester,
(B1.28) sethoxydim,
(B1.29) cycloxydim,
(B1.30) clethodim and
(B1.31) clefoxidim
as herbicidally active combination compound of the group (B1), alone or in combination with the abovementioned active compounds, and
where in the case of the active compound (A1.7), it is also possible to use
(B1.28) sethoxydim,
(B1.29) cycloxydim,
(B1.30) clethodim and
(B1.31) clefoxidim
as herbicidally active combination compound of the group (B1), alone or in combination with the abovementioned active compounds, and
where in the case of the active compound (A2.1), (A2.2), (A2.3) or (A2.4) it is also possible to use structurally different herbicides selected from the group consisting of
(B1.28) sethoxydim,
(B1.29) cycloxydim,
(B1.30) clethodim and
(B1.31) clefoxidim
as herbicidally active combination compound of the group (B1), alone or in combination with the abovementioned active compounds.

Among the abovementioned combinations, preference is given to those in which herbicides from the group (A) are combined with those herbicides from the group (B) which are not listed in the group (A).

Particular preference is given to herbicide combinations (A)+(B1) according to the invention which comprise the following active compounds:
(A1.1)+(B1.1), (A1.1)+(B1.2), (A1.1)+(B1.3), (A1.1)+(B1.4), (A1.1)+(B1.5), (A1.1)+(B1.6), (A1)+(B1.7), (A1.1)+(B1.8), (A1.1)+(B1.9), (A1.1)+(B1.10), (A1.1)+(B1.11), (A1.1)+(B1.12), (A1.1)+(B1.13), (A1.1)+(B1.14), (A1.1)+(B1.15), (A1.1)+(B1.16), (A1.1)+(B1.17), (A1.1)+(B1.18), (A1.1)+(B1.19), (A1.1)+(B1.20) or (A1.1)+(B1.21) or else (A1.1)+(B1.24) or (A1.1)+(B1.25).

In each case, the preferred compound (A1.1) is fenoxaprop-P-ethyl.

The active compounds which belong in each case to the same chemical class form, in the group (B1) and in the groups (B2) to (B4) illustrated further below, in each case preferred subgroups, because they are particularly similar to one another in some use properties.

Thus, the abovementioned active compounds (B1.1) to (B1.8) are anilides or chloroacetanilides which are active mainly against harmful grasses, for example annual grasses, and can be used in rice. Additionally, butachlor and pretilachlor also cover some broad-leaved weeds in rice,
naproanilide, propanil and etobenzanide have as activity spectrum, in addition to grass-like species such as *Echinochloa* spp., *Digitaria* spp., *Setaria* spp., *Panicum* spp., also broad-leaved weeds, such as *Amaranthus* spp.

The compounds (B1.9) to (B1.12) are thiocarbamates, with the emphasis on the use against *Echinochloa* spp. in rice.

The compound (B1.13) belongs to the chemical class of the quinolinecarboxylic acids and is preferably used against weed grasses such as *Echinochloa* spp. and other weeds in rice.

The compound (B1.14) is a benzoylcyclohexanedione which can be used not only against weed grasses, but also against a broader spectrum of weeds in rice.

The compound (B1.17) from the tetrazole series is particularly suitable for controlling weed grasses in rice.

The compounds (B1.16) and (B1.22) are organophosphorus compounds and are particularly suitable for controlling annual grasses and seeds in rice.

The compound (B1.17) from the group of the ureas is suitable for controlling annual and perennial weed grasses in rice.

The compound (B1.18) from the pyridine series is suitable for use against annual grasses in rice.

The compound (B1.19) is particularly effective against weed grasses, sedges and some broad-leaved weeds in rice.

The compound (B1.20) is employed for controlling important weed grasses in rice.

The compound (B1.21) is a grass herbicide against annual harmful plants in rice by the pre- and post-emergence method.

The compound (B1.22) is a grass herbicide against annual grasses and also sedges in transplanted rice by the pre- and post-emergence method.

(B2) Herbicides which are selective in rice, mainly against dicotyledonous harmful plants and cyperaceae, are, for example, one or more compounds selected from the group consisting of
(B2.1) dicamba (PM, pp. 356-357), i.e. 3,6-dichloro-o-anisic acid and its salts,
(B2.2) carfentrazone and its esters, such as carfentrazone-ethyl (PM, pp. 191-193) (=(RS)-2-chloro-3-[2-chloro-5-(4-difluoromethyl-4,5-dihydro-3-methyl-5-oxo-1H-1,2,4-triazol-1-yl)-4-fluorophenyl]propionic acid and its esters, such as the ethyl ester),
(B2.3) picloram (PM, pp. 977-979) (=4-amino-3,5,6-trichloropyridine-2-carboxylic acid) and its salts, such as the potassium salt,
(B2.4) tritosulfuron (CAS Reg. No. 142469-14-5; (see AG Chem New Compound Review, Vol. 17, 1999, p. 24, published by AGRANOVA)) (=N-[[[4-methoxy-6-(trifluoromethyl)-1,3,5-triazin-2-yl]amino]carbonyl]-2-(trifluoromethyl)benzenesulfonamide), and
where in the case of the active compound (A1.3), (A1.4), (A1.5), (A1.6), (A2.1), (A2.2), (A2.3) or (A2.4), it is also possible to use (B2.5) acifluorfen (PM, pp. 12-14) and its salts, such as the sodium salt (=5-[2-chloro-4-(trifluoromethyl)phenoxy]-2-nitrobenzoic acid or its salts, such as the Na salt), (B2.6) 2,4-D (PM, pp. 323-327) (=(2,4-dichlorophenoxy) acetic acid) and its esters and salts, (B2.7) MCPA (PM, pp. 767-769) (=(4-chloro-2-methylphenoxy)acetic acid) and its esters and salts, (B2.8) mecoprop or mecoprop-P (=(RS)— or (R)-2-(4-chloro-o-tolyloxy)propionic acid) and its esters and salts (PM, pp. 776-777), (B2.9) chlorimuron and its esters, such as chlorimuron-ethyl (PM, pp. 217-218) (=2-(4-chloro-2-methoxypyrimidin-2-ylcarbamoylsulfamoyl)benzoic acid and its esters, such as the ethyl ester), (B2.10) triasulfuron (PM, pp. 1222-1224) (=1-[2-(2-chloroethoxy)phenylsulfonyl]-3-(4-methoxy-6-methyl-1,3,5-triazin-2-yl)urea) and (B2.11) ioxynil (PM pp. 718-721) (=4-hydroxy-3,5-diiodobenzonitrile) and its salts and esters as herbicidally active combination compound of the group (B2), alone or in combination with the abovementioned active compounds, and where in the case of the active compound (A1.1), it is also possible to use (B2.5) acifluorfen (PM, pp. 12-14) and its salts, such as the sodium salt (=5-[2-chloro-4-(trifluoromethyl)phenoxy]-2-nitrobenzoic acid or its salts, such as the Na salt)

as herbicidally active combination compound of the group (B2), alone or in combination with the abovementioned active compounds.

Particular preference is given to herbicide combinations (A)+(B2) according to the invention which comprise the following active compounds:

(A1.1)+(B2.1), (A1.1)+B2.2), (A1.1)+(B2.3), (A1.1)+(B2.4) or (A1.1)+(B2.5). The preferred compound (A1.1) is in each case fenoxaprop-P-ethyl.

(B3) Herbicides which are selective in rice, mainly against cyperaceae, are, for example, one or more compounds selected from the group consisting of (B3.1) triclopyr and its esters and salts (=3,5,6-trichloro-2-pyridyloxyacetic acid and its salts and esters), (B3.2) benfuresate (PM, pp. 98-99) (=2,3-dihydro-3,3-dimethylbenzofuran-5-yl ethanesulfonate) and (B3.3) daimuron (PM, p. 330) (=1-(1-methyl-1-phenylethyl)-3-p-tolylurea, where in the case of the active compound (A1.3), (A1.4), (A1.5), (A1.6), (A2.1), (A2.2) or (A2.3) or (A2.4)

(B3.4) bentazone (PM, pp. 109-111) (=3-isopropyl-1H-2,1,3-benzothiadiazin-4-(3H)-one 2,2-dioxide) is suitable.

Particular preference is given to herbicide combinations (A)+(B3.3) according to the invention which comprise the following active compounds:

(A1.1)+(B3.1), (A1.1)+(B3.2) or (A1.1)+(B3.3). The preferred compound (A1.1) is in each case fenoxaprop-P-ethyl.

(B4) Herbicides which are selective in rice, mainly against monocotyledonous and dicotyledonous harmful plants and cyperaceae, are, for example, one or more compounds selected from the group consisting of (B4.1) pendimethalin (PM, pp. 937-939) (N-(1-ethylpropyl)-2,6-dinitro-3,4-xylidine), (B4.2) clomazone (PM, pp. 256-257) (=2-(2-chlorobenzyl)-4,4-dimethyl-1,2-oxazolidin-3-one), (B4.3) benzofenap (PM, pp. 111-112) (=2-[4-(2,4-dichloro-m-toluoyl)-1,3-dimethylpyrazol-5-yloxy]-4'-methylacetophenone), (B4.4) pyrazolynate (PM, pp. 1049-1050) (=4-(2,4-dichlorobenzoyl)-1,3-dimethylpyrazol-5-yl toluene-4-sulfonate), (B4.5) pyrazoxfen (PM, pp. 1054-1055) (=2-[4-(2,4-dichlorobenzoyl)-1,3-dimethylpyrazol-5-yloxy]acetophenone), (B4.6) bispyribac, bispyribac-Na (KIH 2023) (PM, pp. 129-131) (=sodium 2,6-bis-(4,6-dimethoxy-2-pyrimidin-2-yloxy)benzoate), (B4.7) pyriminobac (KIH 6127) (PM, pp. 1071-1073) (=2-(4,6-dimethoxy-2-pyrimidinyloxy)-6-(1-methoxyiminoethyl)benzoic acid) and its salts and esters, such as the methyl ester, (B4.8) oxadiazon (PM, pp. 905-907) (=3-tert-butyl-3-(2,4-dichloro-5-isopropoxyphenyl)-1,3,4-oxadiazol-2(3H)-one), (B4.9) oxadiargyl (PM, pp. 904-905) (=5-tert-butyl-3-[2,4-dichloro-5-(prop-2-ynyloxy)phenyl]-1,3,4-oxadiazol-2 (3H)-one), (B4.10) acetochlor (PM, pp. 10-12) (=2-chloro-N-(ethoxymethyl)-N-(2-ethyl-6-methylphenyl)acetamide), (B4.11) metolachlor (PM, pp. 833-834) (=2-chloro-N-(2-ethyl-6-methylphenyl)-N-(2-methoxy-1-methylethyl)acetamide), (B4.12) metosulam (PM, pp. 836-838) (=2',6'-dichloro-5,7-dimethoxy-3'-methyl[1,2,4]triazolo[1,5-a]pyrimidine-2-sulfonanilide), (B4.13) dalapon (PM, pp. 331-333) (=2,2-dichloropropionic acid) and its salts, such as the sodium salt, (B4.14) cinosulfuron (PM, pp. 248-250) (=1-(4,6-dimethoxy-1,3,5-triazin-2-yl)-3-[2-(2-methoxyethoxy) phenylsulfonyl]urea, (B4.15) pyrazosulfuron and its esters, such as pyrazosulfuron-ethyl (PM, pp. 1052-1054) (=5-(4,6-dimethoxypyrimidin-2-ylcarbamoylsulfamoyl)-1-methyl-pyrazol-4-carboxylic acid) or its salts and esters, such as the ethyl ester, (B4.16) imazosulfuron (PM, pp. 703-704) (=1-(2-chloroimidazol[1,2-a]pyridin-3-ylsulfonyl)-3-(4,6-dimethoxypyrimidin-2-yl)urea), (B4.17) cyclosulfamuron (PM, pp. 288-289) (=1-(2-(cyclopropyl-carbonyl)phenylsulfamoyl]-3-(4,6-dimethoxypyrimidin-2-yl)urea), (B4.18) azimsulfuron (PM, pp. 63-65) (=1-(4,6-dimethoxypyrimidin-2-yl)-3-[1-methyl-4-(2-methyl-2H-tetrazol-5-yl)-pyrazol-5-ylsulfonyl]urea), (B4.19) nicosulfuron (PM, pp. 877-879), i.e. 2-(4,6-dimethoxypyrimidin-2-yl)-3-(3-dimethylcarbamoyl-2-pyridylsulfonyl)urea and its salts, (B4.20) prometryn (PM, pp. 1011-1013) (N,N'-bis-(1-methylethyl)-6-(methylthio)-1,3,5-triazine-2,4-diamine), (B4.21) simetryn (PM, pp. 1108-1109) (N,N'-diethyl-6-(methylthio)-1,3,5-triazine-2,4-diamine), (B4.22) thiazopyr (PM, pp. 1185-1187) (=methyl 2-difluoromethyl-5-(4,5-dihydro-1,3-thiazol-2-yl)-4-isobutyl-6-trifluoromethylnicotinate), (B4.23) pentoxazone (KPP 314) (PM, pp. 942-943)(=3-(4-chloro-5-cyclopentyloxy-2-fluorophenyl)-5-isopropyliden-1,3-oxazolidine-2,4-dione), (B4.24) indanofan (PM, pp. 715) (=(RS)-2-[2-(chlorophenyl)-2,3-epoxypropyl]-2-ethylindane-1,3-dione), (B4.25) pyribenzoxim (LGC 40863) (=2,6-bis(4,6-dimethoxypyridin-2-yl)-1-N-(diphenylmethyl)iminooxycarbonyl]benzene), introduced at the Brighton Crop Protection Conference Weeds 1997, (B4.26) oxaziclomefone (=MY-100=3-[1-(3,5-dichlorophenyl)-1,1-dimethyl]-6-methyl-5-phenyl-2H,3H-1,3-oxazin-4-one (from Rhone Poulenc)), (B4.27) fluthiamide (fenfenacet, BAY FOE 5043; PM, pp. 82-83) (=N-(4-fluorophenyl)-N-(1-methylethyl)-2-[(trifluoromethyl)-1,3,4-thiadiazol-2-yloxy]acetamide), (B4.28) sulfentrazone (PM, pp. 1126-1127) (=N-[2,4-dichloro-5-(4-difluoromethyl-4,5-dihydro-3-methyl-5-oxo-1H-1,2,4-triazol-1-yl)-phenyl]methanesulfonamide) and (B4.29) esprocarb (PM, pp. 472-473) (=S-benzyl 1,2-dimethylpropyl-(ethyl)thiocarbamate), where in the case of the active compound (A1.1), (A1.3), (A1.4), (A1.5), (A1.6), (A2.1), (A2.2) or (A2.3), it is also possible to use (B4.30) oxyfluorfen (PM, pp. 919-921) (=2-chloro-1-(3-ethoxy-4-nitrophenoxy)-4-(trifluoromethyl)benzene)

as herbicidally active combination compound of the group (B4), alone or in combination with the abovementioned active compounds, and where in the case of the active compound (A1.2), (A1.3), (A1.4), (A1.5), (A1.6), (A2.1), (A2.2) or (A2.3), it is also possible to use (B4.31) bensulfuron-methyl (PM, pp. 104-105) (=methyl 2-[[[[[(4,6-dimethoxy-2-pyrimidinyl)amino]carbonyl]amino]sulfonyl]methyl]benzoate), (B4.32) ethoxysulfuron (PM, pp. 488-489) (=1-(4,6-dimethoxypyrimidin-2-yl)-3-(2-ethoxyphenoxysulfonyl) urea, (B4.33) metsulfuron and its esters, such as the methyl ester (PM, pp. 842-844) (=2-[[[[(4-methoxy-6-methyl-1,3,5-triazin-2-yl)-amino]carbonyl]amino]sulfonyl]benzoic acid and its esters, such as the methyl ester) and (B4.34) chlorsulfuron (PM, pp. 239-240) (=1-(2-chlorophenylsulfonyl)-3-(4-methoxy-6-methyl-1,3,5-triazin-2-yl) urea)

as herbicidally active combination compound of the group (B4), alone or in combination with the abovementioned active compounds.

Particular preference is given to herbicide combinations (A)+(B4) according to the invention which comprise the following active compounds:

(A1.1)+(B4.1), (A1.1)+(B4.2), (A1.1)+(B4.3), (A1.1)+(B4.4), (A1.1)+(B4.5), (A1.1)+(B4.6), (A1.1)+(B4.7), (A1.1)+(B4.8), (A1.1)+(B4.9), (A1.1)+(B4.10), (A1.1)+(B4.11), (A1.1)+(B4.12), (A1.1)+(B4.13), (A1.1)+(B4.14), (A1.1)+(B4.15), (A1.1)+(B4.16), (A1.1)+(B4.17), (A1.1)+(B4.18), (A1.1)+(B4.19), (A1.1)+(B4.20), (A1.1)+(B4.21), (A1.1)+(B4.22), (A1.1)+(B4.23), (A1.1)+(B4.24), (A1.1)+(B4.25), (A1.1)+(B4.26), (A1.1)+(B4.27), (A1.1)+(B4.28), (A1.1)+(B4.29) or (A1.1)+(B4.30).

In each case, the preferred compound (A1.1) is fenoxaprop-P-ethyl.

When the short form of the common name is used, this includes all customary derivatives, such as the esters and salts, in particular the commercially available form or forms. In the case of sulfonylureas, salts include those which are formed by exchanging a hydrogen atom at the sulfonamide group for a cation.

The application rates of the herbicides (B) are known in principle and are generally in the range from 1 g to 5000 g of AS/ha (g of AS/ha=g of active substance per hectare). Compounds (B) are preferably employed:

(B1) in amounts of from 10 to 4000, in particular 50-1000 g of AS/ha, (B2.1) to (B2.5) in amounts of from 5 to 1000, in particular 10-500 g of AS/ha, (B2.6-B2.8) in amounts of from 100 to 3000, in particular 200-2000 g of AS/ha;

(B2.9-B2.10) in amounts of from 1 to 50, in particular 4-20 g of AS/ha;

(B2.11) in amounts of from 1 to 2000, in particular 5 to 1000 g of AS/ha;

(B3) in amounts of from 50 to 2500, in particular 100-1000 g of AS/ha;

(B4.1-B4.9) in amounts of from 50 to 5000, in particular 100-2500 g of AS/ha;

(B4.10-B4.13) in amounts of from 15 to 2000, in particular 30-1000 g of AS/ha;

(B4.14-B4.19) in amounts of from 2-80, in particular 4-40 g of AS/ha;

(B4.20-B4.26) in amounts of from 15-2000, in particular 30-1000 g of AS/ha;

(B4.27-B4.29) in amounts of from 5-1000, in particular 10-500 g of AS/ha;

(B4.30) in amounts of from 15-2000, in particular 30-1000 g of AS/ha;

(B4.31-B4.34) in amounts of from 2-80, in particular 4-40 g of AS/ha.

In the context of the abovementioned application rates, lower application rates of the respective active compound are required in the mixtures according to the invention, compared to the individual application. The ratios (A):(B) are, depending on the effective application rates, generally in the range from 1:200 to 200:1, preferably from 1:100 to 100:1, in particular in the range from 1:50 to 50:1.

Preference is given to herbicide combinations of one or more compounds (A) with one or more structurally different compounds selected from the group consisting of (B1) or (B2) or (B3) or (B4).

Furthermore, preference is given to combinations of compounds (A) with one or more components (B) according to the scheme:

(A)+(B1)+(B2), (A)+(B1)+(B3), (A)+(B1)+(B4), (A)+(B2)+(B3), (A)+(B2)+(B4), (A)+(B3)+(B4), (A)+(B1)+(B2)+(B3), (A)+(B1)+(B2)+(B4), (A)+(B1)+(B3)+(B4).

Furthermore, the combinations according to the invention can be employed together with other active compounds, for example from the group of the safeners, fungicides, insecticides and plant growth regulators, or from the group of the additives and formulation auxiliaries which are customary in crop protection.

Additives are, for example, fertilizers and colorants. Of particular importance here are those combinations to which one or more other active compounds of a different structure or safeners [active compounds (C)] are added, for example according to the scheme:

(A)+(B1)+(C), (A)+(B2)+(C) or (A)+(B3)+(C), (A)+(B4)+(C), (A)+(B1)+(B2)+(C), (A)+(B1)+(B3)+(C), (A)+(B1)+(B4)+(C), (A)+(B2)+(B3)+(C), (A)+(B2)+(B4)+(C), (A)+(B3)+(B4)+(C), (A)+(B1)+(B2)+B3)+(C), (A)+(B1)+(B2)+(B4)+(C), (A)+(B1)+(B3)+(B4)+(C), (A)+(B2)+(B3)+(B4)+(C) or (A)+(B1)+(B2)+(B3)+(B4)+(C).

For combinations of the last-mentioned kind with three or more active compounds, the preferred conditions explained below in particular for two-component combinations according to the invention primarily apply likewise if they comprise the two-compound combinations according to the invention, and with respect to the two-component combination in question.

In some cases, even combinations of different active compounds from group (A) are synergistic, so that, based on these two-compound combinations, it is possible to obtain particularly favorable three-compound combinations with additional synergistic effects.

The active compounds (A) are suitable for controlling the weed spectrum in rice crops, for example of transplanted or sown rice. Moreover, they can, if appropriate, be employed for controlling harmful plants in other crops, for example in economically important crops, such as cereals (wheat, barley, rye, maize), sugarbeet, sugar cane, rapeseed, cotton and soybeans. When using the active compounds (A) and (B) in crops such as rice crops, it is advantageous, depending on the crop, to apply a safener above certain application rates to reduce or avoid damage to the crop plant. The following groups of compounds are, for example, suitable as safeners for the abovementioned herbicidally active compounds (A):

a) Compounds of the type of dichlorophenylpyrazoline-3-carboxylic acid, preferably compounds such as ethyl 1-(2, 4-dichlorophenyl)-5-(ethoxycarbonyl)-5-methyl-2-pyrazoline-3-carboxylate (S1-1) ("mefenpyr-diethyl", PM, pp. 781-782), and related compounds, as described in WO 91/07874, b) Derivatives of dichlorophenylpyrazole carboxylic acid, preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carbooxylate (S1-3), ethyl 1-(2,4-dichlorophenyl)-5-(1,1-dimethylethyl) pyrazole-3-carboxylate (S1-4), ethyl 1-(2,4-dichlorophenyl)-5-phenylpyrazole-3-carboxylate (S1-5) and related compounds as described in EP-A-333 131 and EP-A-269 806.

c) Compounds of the type of the triazolecarboxylic acids, preferably compounds such as fenchlorazole(ethyl ester), i.e. ethyl 1-(2,4-dichlorophenyl)-5-trichloromethyl-(1H)-1,2,4-triazole-3-carboxylate (S1-6) and related compounds as described in EP-A-174 562 and EP-A-346 620.

d) Compounds of the type of the 5-benzyl- or 5-phenyl-2-isoxazoline-3-carboxylic acid, or the 5,5-diphenyl-2-isoxazoline-3-carboxylic acid, preferably compounds such as ethyl 5-(2,4-dichlorobenzyl)-2-isoxazoline-3-carboxylate (S1-7) or ethyl 5-phenyl-2-isoxazoline-3-carboxylate (S1-8) and related compounds, as described in WO 91/08202, or ethyl 5,5-diphenyl-2-isoxazolinecarboxylate (S1-9) ("isoxadifen-ethyl") or its -n-propyl ester (S1-10) or ethyl 5-(4-fluorophenyl)-5-phenyl-2-isoxazoline-3-carboxylate (S1-11), as described in the German patent application (WO-A-95/07897).

e) Compounds of the type of the 8-quinolineoxyacetic acid (S2), preferably 1-methylhex-1-yl (5-chloro-8-quinolineoxy)acetate (common name "cloquintocet-mexyl" (S2-1) (see PM, pp. 263-264) 1,3-dimethylbut-1-yl (5-chloro-8-quinolineoxy)acetate (S2-2), 4-allyloxybutyl (5-chloro-8-quinolineoxy)acetate (S2-3), 1-allyloxyprop-2-yl (5-chloro-8-quinolineoxy)acetate (S2-4), ethyl (5-chloro-8-quinolineoxy)acetate (S2-5), methyl (5-chloro-8-quinolineoxy)acetate (S2-6), allyl (5-chloro-8-quinolineoxy)acetate (S2-7), 2-(2-propylideneiminoxy)-1-ethyl (5-chloro-8-quinolineoxy)acetate (S2-8), 2-oxoprop-1-yl (5-chloro-8-quinolineoxy)acetate (S2-9) and related compounds, as described in EP-A-86 750, EP-A-94 349 and EP-A-191 736 or EP-A-0 492 366.

f) Compounds of the type of the (5-chloro-8-quinolineoxy) malonic acid, preferably compounds such as diethyl (5-chloro-8-quinolineoxy)malonate, diallyl (5-chloro-8-quinolineoxy)malonate, methyl ethyl (5-chloro-8-quinolineoxy)malonate and related compounds, as described in EP-A-0 582 198.

g) Active compounds of the type of the phenoxyacetic or -propionic acid derivatives or the aromatic carboxylic acids, such as, for example, 2,4-dichlorophenoxyacetic acid (esters) (2,4-D), 4-chloro-2-methylphenoxypropionic acid (esters) (Mecoprop), MCPA or 3,6-dichloro-2-methoxybenzoic acid (esters) (Dicamba).

The abovementioned safeners are in many cases also suitable for active compounds of group (B). Moreover, the following safeners are suitable for the herbicide combinations according to the invention in rice and other cereal crops, such as for example, wheat, maize, millet, etc.:

h) Active compounds of the type of the pyrimidines, which are used as soil-acting safeners in rice, such as, for example,
"fenclorim" (PM, pp. 512-511) (=4,6-dichloro-2-phenylpyrimidine), which is known as safener for pretilachlor in sown rice, i) Active compounds of the type of the pyrimidines, which are used as soil-acting safeners in rice, such as, for example,
"fenclorim" (PM, pp. 512-511) (=4,6-dichloro-2-phenylpyrimidine), which is known as safener for damage caused by pretilachlor in sown rice j) Active compounds of the type of the dichloroacetamides, which are frequently used as pre-emergent safeners (soil-acting safeners), such as, for example,
"dichlormid" (PM, pp. 363-364) (=N,N-diallyl-2,2-dichloroacetamide),
"R-29148" (=3-dichloroacetyl-2,2,5-trimethyl-1,3-oxazolidine from Stauffer),
"benoxacor" (PM, pp. 102-103) (=4-dichloroacetyl-3,4-dihydro-3-methyl-2H-1,4-benzoxazine),
"PPG-1292" (=N-allyl-N-[(1,3-dioxolan-2-yl)methyl] dichloroacetamide from PPG Industries),
"DK-24" (=N-allyl-N-[(allylaminocarbonyl)methyl] dichloroacetamide from Sagro-Chem),
"AD-67" or "MON 4660" (=3-dichloroacetyl-1-oxa-3-aza-spiro[4,5]decane from Nitrokemia or Monsanto),
"diclonon" or "BAS145138" or "LAB145138" (=3-dichloroacetyl-2,5,5-trimethyl-1,3-diazabicyclo[4.3.0] nonane from BASF) and
"furilazol" or "MON 13900" (see PM, 637-638) (=(RS)-3-dichloroacetyl-5-(2-furyl)-2,2-dimethyloxazolidine)

k) Active compounds of the type of the dichloroacetone derivatives, such as, for example,
"MG 191" (CAS-Reg. No. 96420-72-3) (=2-dichloromethyl-2-methyl-1,3-dioxolane from Nitrokemia), which is known as safener for maize, l) Active compounds of the type of the oxyimino compounds, which are known as seed dressings, such as, for example,
"oxabetrinil" (PM, pp. 902-903) (=(Z)-1,3-dioxolan-2-ylmethoxy-imino(phenyl)acetonitrile), which is known as seed dressing safener for millet against metolachlor damage,
"fluxofenim" (PM, pp. 613-614) (=1-(4-chlorophenyl)-2, 2,2-trifluoro-1' ethanone O-(1,3-dioxolan-2-ylmethyl) oxime), which is known as seed dressing safener for millet against metolachlor damage,
"cyometrinil" or "-CGA-43089" (PM, p. 1304) (=(Z)-Cyanomethoxyimino(phenyl)acetonitrile), which is known as seed dressing safener for millet against metolachlor damage, m) Active compounds of the type of the thiazolecarboxylic esters, which are known as seed dressings, such as, for example,
"flurazol" (PM, pp. 590-591) (=benzyl 2-chloro-4-trifluoromethyl-1,3-thiazole-5-carboxylate), which is known as seed dressing safener for millet against alachlor and metolachlor damage, n) Active compounds of the type of the naphthalenedicarboxylic acid derivatives, which are known as seed dressings, such as, for example, "naphthalic anhydride" (PM, p. 1342) (=1,8-naphthalene-dicarboxylic anhydride), which is known as seed dressing safener for maize against thiocarbamate herbicide damage, o) Active compounds of the type of the chromanacetic acid derivatives, such as, for example,
"CL 304415" (CAS-Reg. No. 31541-57-8) (=2-(4-carboxychroman-4-yl)acetic acid from American Cyanamid), which is known as safener for maize against imidazolinone damage, p) Active compounds which, in addition to a herbicidal action against harmful plants, also have safener action in crop plants such as rice, such as, for example,
"dimepiperate" or "MY-93" (PM, pp. 404-405) (=S-1-methyl-1-phenylethyl piperidine-1-thiocarboxylate), which is known as safener for rice against herbicide molinate damage,
"daimuron" or "SK 23" (PM, p. 330) (=1-(1-methyl-1-phenylethyl)-3-p-tolylurea), which is known as safener for rice against herbicide imazosulfuron damage,
"cumyluron"="JC-940" (=3-(2-chlorophenylmethyl)-1-(1-methyl-1-phenylethyl)urea, see JP-A-60087254), which is known as safener for rice against damage by some herbicides,
"methoxyphenon" or "NK 049" (=3,3'-dimethyl-4-methoxy-benzophenone), which is known as safener for rice against damage by some herbicides,
"CSB" (=1-bromo-4-(chloromethylsulfonyl)benzene) (CAS-Reg. No. 54091-06-4 from Kumiai), which is known as safener against damage by some herbicides in rice.

Among the abovementioned safeners, (S1-1), (S1-9) and (S2-1), in particular (S1-9), are of particular interest.

Some of the safeners are already mentioned above as herbicides and consequently show, in addition to the herbicidal action against harmful plants, also protective action in the case of the crop plants.

The invention furthermore provides the following specific two-compound and multi-compound combinations with herbicides and/or safeners:

Active compound fenoxaprop (A1.1)+safener (S1-9)+thiazopyr
Active compound fenoxaprop (A1.1)+safener (S1-9)+clomazone
Active compound fenoxaprop (A1.1)+safener (S1-9)+benthiocarb
Active compound fenoxaprop (A1.1)+safener (S1-9)+butachlor
Active compound fenoxaprop (A1.1)+safener (S1-9)+quinchlorac
Active compound fenoxaprop (A1.1)+safener (S1-9)+pendimethalin
Active compound fenoxaprop (A1.1)+safener (S1-9)+oxadiargyl
Active compound fenoxaprop (A1.1)+safener (S1-9)+oxadiazon
Active compound fenoxaprop (A1.1)+safener (S1-9)+cafenstrol
Active compound fenoxaprop (A1.1)+safener (S1-9)+bispyribac
Active compound fenoxaprop (A1.1)+safener (S1-9)+metosulam
Active compound fenoxaprop (A1.1)+safener (S1-9)+carflutrazon
Active compound fenoxaprop (A1.1)+safener (S1-9)+ethoxysulfuron
Active compound fenoxaprop (A1.1)+ethoxysulfuron+anilofos
Active compound fenoxaprop (A1.1)+ethoxysulfuron+quinchlorac
Active compound fenoxaprop (A1.1)+ethoxysulfuron+molinate
Active compound fenoxaprop (A1.1)+bensulfuron-methyl+quinchlorac
Active compound fenoxaprop (A1.1)+bensulfuron-methyl+molinate The abovementioned multi-compound combinations have synergies with respect to the herbicidal action and selectivity and a favorable action with respect to the weed spectrum. Instead of the safener (S1-9) other safeners can often likewise be applied, preferably the safeners of the above-mentioned groups a) through e).

The combinations according to the invention (=herbicidal compositions) have excellent herbicidal activity against a broad spectrum of economically important mono- and dicotyledonous harmful plants, as encountered, preferably, in crops of rice. The active compounds also act efficiently on perennial weeds which produce shoots from rhizomes, root stocks or other perennial organs and which are difficult to control. In this context, it is immaterial whether the substances are applied pre-sowing, pre-emergence or post-emergence. Preference is given to the application by the post-emergence method or the early post-sowing/pre-emergence method.

Specifically, examples may be mentioned of some representatives of the monocotyledonous and dicotyledonous weed flora which can be controlled by the compounds according to the invention, without these being a restriction to certain species.

Among the monocotyledonous weed species, the active compounds act efficiently against, for example, *Echinochloa* spp., *Brachiaria* spp., *Leptochloa* spp. and *Digitaria* spp., but also against *Panicum* spp., *Agropyron* spp., wild cereal forms and *Sorghum* spp., *Setaria* spp., *Alopecurus* spp., *Avena* spp., *Apera spica venti*, *Lolium* spp., *Phalaris* spp. *Cynodon* spp., *Poa* spp. and *Cyperus* species and *Imperata*.

In the case of the dicotyledonous weed species, the spectrum of action extends to species such as, for example, *Amaranthus* spp., *Sphenoclea* spp., *Heteranthera* spp., *Eleocharis* spp., *Ipomoea* spp., *Eschynomena* spp., *Sesbania* spp. and *Cyperrus* spp., but also *Polygonum* spp., *Xanthium* spp., *Equisetum*, *Chenopodium* spp., *Abutilon* spp., *Anthemis* spp., *Lamium* spp., *Matricaria* spp., *Stellaria* spp., *Kochia* spp., *Viola* spp., *Datura* spp., *Chrysanthemum* spp., *Thlaspi* spp., *Pharbitis* spp., *Sida* spp., *Sinapis* spp., *Cupsella* spp., *Ambrosia* spp., *Galium* spp., *Emex* spp., *Lamium* spp., *Papaver* spp., *Solanum* spp., *Cirsium* spp., *Veronica* spp., *Convolvulus* spp., *Rumex* and *Artemisia*.

If the compounds according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely.

If the active compounds are applied post-emergence to the green parts of the plants, growth also stops drastically a very short time after the treatment and the weed plants remain at the developmental stage of the point in time of application, or they die completely after a certain time, so that in this manner competition by the weeds, which is harmful to the crop plants, is eliminated at a very early point in time and in a sustained manner.

The herbicidal compositions according to the invention have a rapid and long-lasting herbicidal action. The shower resistance of the active compounds in the combinations according to the invention is generally favorable. It is a particular advantage that the effective dosages of compounds (A) and (B) used in the combinations can be adjusted to such a low level, that their soil action is optimally low. Thus, it is not only possible to use them in sensitive crops, but groundwater contaminations are virtually avoided. By using the active compound combination according to the invention, it is possible to reduce the required application rate of the active compounds considerably.

When herbicides of type (A)+(B) are applied jointly, super additive (=synergistic) effects are observed. Here, the activity in the combinations is stronger than the expected sum of the activities of the individual herbicides used. The synergistic effects permit a reduction of the application rate, the control of a broader spectrum of broad-leaved weeds and weed grasses, a more rapid onset of the herbicidal action, a longer duration of action, a better control of the harmful plants with only one or a few applications and a widening of the possible period of use. In some cases, the use of compositions also reduces the amount of harmful ingredients, such as nitrogen or oleic acid, and their incorporation into the soil.

The abovementioned properties and advantages are needed in practical control of weeds to keep agricultural crops free of undesirable competing plants and thus to secure and/or increase the quality and quantity of the yields. With respect to the described properties, the prior art is considerably surpassed by these novel combinations.

Although the compounds according to the invention have an excellent herbicidal activity against monocotyledonous and dicotyledonous weeds, the crop plants are not damaged at all, or only to a negligible extent.

In addition, the substances according to the invention have outstanding growth-regulating properties in crop plants. They engage in the plant metabolism in a regulating manner and can thus be employed for the targeted control of plant constituents and for facilitating harvesting, for example by provoking desiccation and stunted growth. Furthermore, they are also suitable for generally regulating and inhibiting undesirable vegetative growth, without destroying the plants in the process. Inhibition of vegetative growth plays an important role in many monocotyledonous and dicotyledonous crops because lodging can be reduced hereby, or prevented completely.

Owing to their herbicidal and plant growth-regulatory properties, the compounds can be employed for controlling harmful plants in known crops or in still to be developed tolerant or genetically engineered plants. The transgenic plants generally have particularly advantageous properties, in addition to resistance to the substances according to the invention, for example resistance to plant diseases or causative organisms of plant diseases, such as certain insects or microorganisms such as fungi, bacteria or viruses. Other particular properties relate, for example, to the quantity, quality, storage-stability, composition and to specific ingredients of the harvested product. Thus, transgenic plants having an increased starch content or a modified quality of the starch or those having a different fatty acid composition of the harvested product are known.

Conventional ways for preparing novel plants which have modified properties compared to known plants comprise, for example, traditional breeding methods and the generation of mutants. Alternatively, novel plants having modified properties can be generated with the aid of genetic engineering methods (see, for example, EP-A 0 221 044, EP-A 0 131 624). For example, there have been described several cases of
  genetically engineered changes in crop plants in order to modify the starch synthesized in the plants (for example WO 92/11376, WO 92/14827, WO 91/19806),
  transgenic crop plants which are resistant to other herbicides, for example sulfonylureas (EP-A 0 257 993, U.S. Pat. No. 5,013,659),
  transgenic crop plants having the ability to produce *Bacillus thuringiensis* toxins (Bt toxins) which impart resistance to certain pests to the plants (EP-A 0 142 924, EP-A 0 193 259),
  transgenic crop plants having a modified fatty acid composition (WO 91/13972).

Numerous molecular biological techniques which allow the preparation of novel transgenic plants having modified properties are known in principle; see, for example. Sambrook et al., 1989, Molecular Cloning, A Laboratory Manual, 2nd ed. Cold Spring Harbor Laboratory Press, Cold Spring Harbor, N.Y.; or Winnacker "Gene und Klone" [Genes and Clones], VCH Weinheim, 2nd edition 1996, or Christou, "Trends in Plant Science" 1 (1996) 423-431). In order to carry out such genetic engineering manipulations, it is possible to introduce nucleic acid molecules into plasmids which allow a mutagenesis or a change in the sequence to occur by recombination of DNA sequences. Using the abovementioned standard processes it is possible, for example, to exchange bases, to remove partial sequences or to add natural or synthetic sequences. To link the DNA fragments with each other, it is possible to attach adaptors or linkers to the fragments.

Plant cells having a reduced activity of a gene product can be prepared, for example, by expressing at least one appropriate antisense-RNA, a sense-RNA to achieve a cosuppression effect, or by expressing at least one appropriately constructed ribozyme which specifically cleaves transcripts of the abovementioned gene product.

To this end it is possible to employ both DNA molecules which comprise the entire coding sequence of a gene product including any flanking sequences that may be present, and DNA molecules which comprise only parts of the coding sequence, it being necessary for these parts to be long enough to cause an antisense effect in the cells. It is also possible to use DNA sequences which have a high degree of homology to the coding sequences of a gene product but which are not entirely identical.

When expressing nucleic acid molecules in plants, the synthesized protein can be localized in any desired compartment of the plant cells. However, to achieve localization in a certain compartment, it is, for example, possible to link the coding region with DNA sequences which ensure localization in a certain compartment. Such sequences are known to the person skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated to whole plants using known techniques. The transgenic plants can in principle be plants of any desired plant species, i.e. both monocotyledonous and dicotyledonous plants. In this manner, it is possible to obtain transgenic plants which have modified properties by overexpression, suppression or inhibition of homologous (=natural) genes or gene sequences or by expression of heterologous (=foreign) genes or gene sequences.

The invention therefore also provides a method for controlling undesirable vegetation, preferably in crops, which comprises applying one or more herbicides of type (A) with one or more herbicides of type (B) onto the harmful plants, parts thereof or onto the area under cultivation.

The invention also provides the use of the novel combinations of compounds (A)+(B) for controlling harmful plants, preferably in crops.

The active compound combinations according to the invention can be present both as mixed formulations of the two components, if appropriate with other active compounds, additives and/or customary formulation auxiliaries, which are then applied in a customary manner diluted with water, or be prepared as so-called tank mixes by joint dilution of the separately formulated or partially separately formulated components with water.

The compounds (A) and (B) or their combinations can be formulated in various ways depending on the prevailing biological and/or chemico-physical parameters. Examples of suitable formulation options are: wettable powders (WP), emulsifiable concentrates (EC), aqueous solutions (SL) emulsions (EW), such as oil-in-water and water-in-oil emulsions, sprayable solutions or emulsions, oil- or water-based dispersions, suspoemulsions, dusts (DP), seed-dressing compositions, granules for broadcasting and soil application, or water-dispersible granules (WG), ULV formulations, microcapsules or waxes.

The individual formulation types are known in principle and are described, for example, in Winnacker-Küchler, "Chemische Technologie" [Chemical Technology], Volume 7, C. Hauser Verlag Munich, 4th. Edition 1986; van Valkenburg, "Pesticides Formulations", Marcel Dekker, N.Y., 1973; K Martens, "Spray Drying Handbook", 3rd Ed. 1979, G. Goodwin Ltd. London.

The necessary formulation auxiliaries, such as inert materials, surfactants, solvents and other additives, are likewise known and are described, for example, in Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1950; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesellschoft, Stuttgart 1976; Winnacker-Küchler, "Chemische Technologie" [Chemical Technology], Volume 7, C. Hauser Verlag Munich, 4th Edition 1986.

Based on these formulations it is also possible to produce combinations with other pesticidally active substances, such as other herbicides, fungicides or insecticides, and also with safeners, fertilizers and/or growth regulators, for example in the form of a ready-mix or tank mix.

Wettable powders are preparations which are uniformly dispersible in water and which contain, in addition to the active compound and as well as a diluent or inert substance, surfactants of ionic or nonionic type (wetting agents, dispersants), for example polyethoxylated alkyl phenols, polyethoxylated fatty alcohols, polyethoxylated fatty amines, alkanesulfonates, alkylbenzenesulfonates, sodium ligninsulfonate, sodium 2,2'-dinaphthylmethane-6,6'-disulfonate, sodium dibutylnaphthalene-sulfonate or else sodium oleoylmethyltaurinate.

Emulsifiable concentrates are prepared by dissolving the active compound in an organic solvent, for example butanol, cyclohexanone, dimethylformamide, xylene or else relatively high-boiling aromatic compounds or hydrocarbons with the addition of one or more surfactants of ionic or nonionic type (emulsifiers). Examples of emulsifiers which can be used are calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products, alkyl polyethers, sorbitan fatty acid esters, polyoxyethylene sorbitan fatty acid esters or polyoxyethylene sorbitan esters.

Dusts are obtained by grinding the active compound with finely divided solid substances, for example talc, natural clays, such as kaolin, bentonite and pyrophyllite, or diatomaceous earth.

Granules can be prepared either by spraying the active compound onto adsorptive, granulated inert material or by applying active-compound concentrates to the surface of carriers such as sand, kaolinites or granulated inert material, by means of adhesive binders, for example polyvinyl alcohol, sodium polyacrylate or else mineral oils. Suitable active compounds can also be granulated in the manner which is customary for the preparation of fertilizer granules, if desired as a mixture with fertilizers.

Water-dispersible granules are generally prepared by processes such as spray-drying, fluidized-bed granulation, disk granulation, mixing using high-speed mixers, and extrusion without solid inert material.

The agrochemical formulations generally contain from 0.1 to 99% by weight, in particular from 2 to 95% by weight, of active compounds of types A and/or B, the following concentrations being customary, depending on the type of formulations:

In wettable powders the concentration of active compound is, for example, from about 10 to 95% by weight, the remainder to 100% by weight consisting of customary formulation constituents. In emulsifiable concentrates the concentration of active compound can be, for example, from 5 to 80% by weight.

Formulations in the form of dusts usually contain from 5 to 20% by weight of active compound, while sprayable solutions contain from about 0.2 to 25% by weight of active compound.

In the case of granules, such as dispersible granules, the content of active compound depends partly on whether the active compound is in liquid or solid form and on the granulation auxiliaries and fillers that are used. In water-dispersible granules the content is generally between 10 and 90% by weight.

In addition, said formulations of active compound may comprise the tackifiers, wetting agents, dispersants, emulsifiers, preservatives, antifreeze agents and solvents, fillers, colorants and carriers, antifoams, evaporation inhibitors and pH and viscosity regulators which are customary in each case.

For use, the formulations, which are in commercially available form, are, if appropriate, diluted in a customary manner, for example using water in the case of wettable powders, emulsifiable concentrates, dispersions and water-dispersible granules. Preparations in the form of dusts, soil granules, granules for spreading and sprayable solutions are conventionally not diluted any further with other inert substances prior to use.

The active compounds can be applied to the plants, parts of the plants, seeds of the plants or the area under cultivation (tilled soil), preferably to the green plants and parts of the plants and, if desired, additionally to the tilled soil.

A possible use is the joint application of the active compounds in the form of tank mixes, where the concentrated formulations of the individual active substances, in the form of their optimal formulations, are mixed jointly with water in the tank, and the spray mixture obtained is applied.

A joint herbicidal formulation of the combination according to the invention of the active compounds (A) and (B) has the advantage that it can be applied more easily because the amounts of the components have already been adjusted to one another in the correct ratio. Moreover, the auxiliaries of the formulation can be selected to suit each other in the best possible way, while a tank mix of various formulations may result in undesirable combinations of auxiliaries.

A. General Formulation Examples a) A dust is obtained by mixing 10 parts by weight of an active compound/active compound mixture and 90 parts by weight of talc as inert substance and comminuting the mixture in a hammer mill.
b) A wettable powder which is readily dispersible in water is obtained by mixing 25 parts by weight of an active compound/active compound mixture, 64 parts by weight of kaolin-containing quartz as inert substance, 10 parts by weight of potassium lignosulfonate and 1 part by weight of sodium oleoylmethyltaurinate as wetting agent and dispersant, and grinding the mixture in a pinned-disk mill.
c) A dispersion concentrate which is readily dispersible in water is obtained by mixing 20 parts by weight of an active compound/active compound mixture with 6 parts by weight of alkylphenol polyglycol ether (®Triton X 207), 3 parts by weight of isotridecanol polyglycol ether (8 EO) and 71 parts by weight of paraffinic mineral oil (boiling range for example approximately 255 to 277° C.) and grinding the mixture in a ball mill to a fineness of below 5 microns.
d) An emulsifiable concentrate is obtained from 15 parts by weight of an active compound/active compound mixture, 75 parts by weight of cyclohexanone as solvent and 10 parts by weight of ethoxylated nonylphenol as emulsifier.
e) Water-dispersible granules are obtained by mixing
   75 parts by weight of an active compound/active compound mixture,
   10 parts by weight of calcium lignosulfonate,
   5 parts by weight of sodium lauryl sulfate,
   3 parts by weight of polyvinyl alcohol and
   7 parts by weight of kaolin,
   grinding the mixture in a pinned-disk mill and granulating the powder in a fluidized bed by spraying on water as granulation liquid.
f) Water-dispersible granules are also obtained by homogenizing and precomminuting, in a colloid mill,
   25 parts by weight of an active compound/active compound mixture,
   5 parts by weight of sodium 2,2'-dinaphthylmethane-6,6'-disulfonate,
   2 parts by weight of sodium oleoylmethyltaurinate,
   1 part by weight of polyvinyl alcohol,
   17 parts by weight of calcium carbonate and
   50 parts by weight of water,
   subsequently grinding the mixture in a bead mill and atomizing and drying the resulting suspension in a spray tower by means of a single-substance nozzle.

B. Biological Examples

1. Pre-Emergence Effect on Weeds

Seeds or rhizome pieces of monocotyledonous and dicotyledonous weed plants are placed in sandy loam soil in pots and covered with soil. The compositions, formulated in the form of concentrated aqueous solutions, wettable powders or emulsion concentrates, are then applied to the surface of the soil cover as aqueous solution, suspension or emulsion at an application rate of 600 to 800 l of water/ha (converted), in various dosages. After the treatment, the pots are placed in a greenhouse and kept under good growth conditions for the weeds. After the test plants have emerged, the damage to the plants or the negative effects on the emergence is scored visually after a test period of 3 to 4 weeks by comparison with untreated controls. As shown by the test results, the compositions according to the invention have good herbicidal pre-emergence activity against a broad spectrum of weed grasses and broad-leaved weeds.

Scoring and evaluation of the synergistic herbicidal effects:

The herbicidal efficacy of the active compounds or active compound mixtures was scored visually using the treated plots in comparison to untreated control plots. The damage and development of all above-ground parts of the plants were recorded. Scoring was carried out using a percentage scale (100% effect=all plants killed; 50% effect=50% of the plants and the green parts of the plants killed; 0% effect=no noticeable effect=like control plot). The scores of in each case 4 plots were averaged.

When using the combinations according to the invention, herbicidal effects on a harmful plant species are frequently observed which exceed the formal sum of the activities of the herbicides contained in the combination when applied on their own.

Alternatively, in some cases, it can be observed that a lower application rate is required for the herbicide combination in order to obtain, compared to the individual preparations, the same effect on a harmful plant species. Such activity increases or increases in effectiveness or reduced application rates are a strong indication of a synergistic effect.

If the observed activity values already exceed the formal sum of the values for the trials with the individual applications, they also exceed the expected value according to Colby which is calculated using the following formula and which is likewise considered to be an indication of synergism (cf. S. R. Colby; in Weeds 15 (1967) pp. 20 to 22):

$$E = A + B - (A \cdot B/100)$$

The figures denote: A, B=activity of the active compounds A or B in % at a or b g of AS/ha; E=expected value in % at a+b g of AS/ha.

The observed test results show, at suitable low dosages, an effect of the combinations which exceeds the expected values according to Colby.

2. Post-Emergence Effect on Weeds

Seeds or rhizome pieces of monocotyledonous and dicotyledonous weeds are placed in sandy loam soil in pots, covered with soil and grown in a greenhouse under good growth conditions (temperature, atmospheric humidity, water supply). Three weeks after sowing, the test plants are treated at the three-leaf stage with the compositions according to the invention. The compositions according to the invention, formulated as wettable powders or as emulsion concentrates, are sprayed, at various dosages, onto the green parts of the plant at an application rate of 600 to 800 l of water/ha (converted). After the test plants have been in the greenhouse for about 3 to 4 weeks under ideal growth conditions, the effect of the preparations is scored visually by comparison with untreated controls. The compositions according to the invention also have a good herbicidal post-emergence activity against a broad spectrum of economically important weed grasses and weeds.

Frequently, activities of the combinations according to the invention are observed which exceed the formal sum of the activities when the herbicides are applied individually. The observed test results show, at suitable low dosages, an effect of the combinations which exceeds the expected values according to Colby (cf. scoring in Example 1).

3. Herbicidal Effect and Crop Plant Compatibility (Field Trials)

Crop plants were grown outdoors on plots under natural outdoor conditions, and seeds or rhizome pieces of typical harmful plants were laid out or the natural weed growth was utilized. Treatment with the compositions according to the invention was carried out after the harmful plants had emerged and the crop plants were, generally, at the 2- to 4-leaf stage; in some cases (as stated), application of individual active compounds or active compound combinations was carried out pre-emergence (cf. Example 1) or as a sequential treatment partly pre-emergence and/or post-emergence.

After the application, for example 2, 4, 6 and 8 weeks after the application, the effect of the preparations was scored visually by comparison with untreated controls (cf. scoring in Example 1). In the field trial as well, the compositions according to the invention have synergistic herbicidal activity against a broad spectrum of economically important weed grasses and broad-leaved weeds. The comparison showed that the combinations according to the invention in most cases have a higher, in some cases a considerably higher, herbicidal activity than the sum of the activities of the individual herbicides, thus indicating synergism. Moreover, the effects in essential phases of the scoring period were above the expected values according to Colby (cf. scoring in Example 1), also indicating synergism. In contrast, the crop plants were, as a consequence of the treatments with the herbicidal compositions, damaged only to a small degree, if at all.

Specific Test Examples

The following abbreviations are used in the tables below: g of AS/ha=Gram of active substance (=100% active compound) per hectare; The expected values according to Colby are in each case given in brackets (E= . . . ).

TABLE 1

Herbicidal effect and selectivity in rice (field trial)

| Active compound(s) | Dose[1] g of AS/ha | Herbicidal effect[2] (%) against SEBEX | AMARE | Damage[2] (in %) to rice |
|---|---|---|---|---|
| (A1.1)[S] | 45 | 0 | 0 | 0 |
| (B4.6) | 45 | 93 | 93 | 0 |
| (A1.1)[S] + (B4.6) | 45 + 45 | 95 (E = 93) | 95 (E = 93) | 0 |

Abbreviations for Table 1:
[1] = application in each case post-emergence,
[2] = scoring 7 days after application
(A1.1)[S] = fenoxaprop-P-ethyl in combination with the safener (S1-9),
(S1-9) = ethyl 5,5-diphenyl-2-isoxazoline carboxylate
(B4.6) = bispyribac-Na (KIH 2023)
SEBEX = *Sesbania* exaltata;
AMARE = *Amaranthus retroflexus*

TABLE 2

Herbicidal effect and selectivity in rice (field trial)

| Active compound(s) | Dose[1] g of AS/ha | Herbicidal effect[2] (in %) against ECHCO | Damage[2] (in %) to rice |
|---|---|---|---|
| (A1.1) | 45 | 51 | 0 |
| (B3.2) | 400 | 0 | 0 |
| (A1.1) + (B3.2) | 45 + 400 | 56 (E = 51) | 0 |

Abbreviations for Table 2:
[1] = application in each case post-emergence at the 2-4-leaf stage,
[2] = scoring 21 days after application
(A1.1) = fenoxaprop-P-ethyl,
(B3.2) = benfuresate
ECHCO = *Echinochloa colona*

TABLE 3

Herbicidal effect and selectivity in rice (field trial)

| Active compound(s) | Dose[1] g of AS/ha | Herbicidal effect[2] (in %) against ECHCO | Damage[2] (in %) to rice |
|---|---|---|---|
| (A1.1) | 45 | 83 | 21 |
| (B4.9) | 25 | 33 | 22 |
|  | 50 | 43 | 23 |
|  | 100 | 48 | 22 |
| (A1.1) + (B4.9) | 45 + 25 | 95 (E = 88) | 36 |

Abbreviations for Table 3:
[1] = application in each case post-emergence at he 2-4-leaf stage,
[2] = scoring 28 days after application
(A1.1) = fenoxaprop-P-ethyl,
(B4.9) = oxadiargyl
ECHCO = *Echinochloa colona*

TABLE 4

Herbicidal effect and selectivity in rice (field trial)

| Active compound(s) | Dose[1] g of AS/ha | Herbicidal effect[2] (in %) against ELEIN | Damage[2] (in %) to rice |
|---|---|---|---|
| (A1.1) | 45 | 80 | 21 |
| (B4.26) | 30 | 0 | 15 |
|  | 60 | 37 | 19 |
| (A1.1) + (84.26) | 45 + 30 | 96 (E = 80) | 24 |

Abbreviations for Table 4:
[1] = application in each case post-emergence at the 2-4-leaf stage,
[2] = scoring 28 days after application
(A1.1) = fenoxaprop-P-ethyl,
(B4.26) = maziclomefone (MY 100)
ELGIN = *Eleusine indica*

TABLE 5

Herbicidal effect and selectivity in rice (greenhouse trial)

| Active compound(s) | Dose[1] g of AS/ha | Herbicidal effect[2] (in %) against SAGPY | Damage[2] (in %) to rice |
|---|---|---|---|
| (A1.1) | 75 | 0 | 8 |
|  | 37.5 | 0 | 0 |

TABLE 5-continued

Herbicidal effect and selectivity in rice (greenhouse trial)

| Active compound(s) | Dose[1] g of AS/ha | Herbicidal effect[2] (in %) against SAGPY | Damage[2] (in %) to rice |
|---|---|---|---|
| (B1.15) | 25 | 0 | 0 |
|  | 50 | 40 | 0 |
|  | 100 | 80 | 0 |
| (A1.1) + (B1.15) | 37.5 + 50 | 75 (E = 40) | .3 |

Abbreviations for Table 5:
[1] = application in each case post-emergence at the 1-2-leaf stage,
[2] = scoring 20 days after application
(A1.1) = fenoxaprop-P-ethyl,
(B1.15) = fentrazamid
SAGPY = Sagittaria pygmaea

TABLE 6

Herbicidal effect and selectivity in rice (greenhouse trial)

| Active compound(s) | Dose[1] g of AS/ha | Herbicidal effect[2] (in %) against ECHCG | Damage[2] (in %) to rice |
|---|---|---|---|
| (A1.1) | 75 | 82 | 3 |
|  | 37 | 40 | 0 |
|  | 18 | 15 | 0 |
| Clefoxidim (B1.31) | 75 | 83 | 0 |
|  | 37 | 10 | 0 |
|  | 18 | 0 | 0 |
| (A1.1) + (B1.31) | 18 + 18 | 65 (E = 15) | .0 |
|  | 18 + 37 | 85 (E = 25) | .0 |
|  | 37 + 18 | 88 (E = 40) | .0 |

Abbreviations for Table 6:
[1] = application in each case post-emergence at the 3-4-leaf stage,
[2] = scoring 20 days after application
(A1.1) = fenoxaprop-P-ethyl,
(B1.31) = clefoxidim
ECHCG = Echinochloa crus-galli

TABLE 7

Herbicidal effect and selectivity in rice (field trial)

| Active compound(s) | Dose[1] g of AS/ha | Herbicidal effect[2] (in %) against AMARE | Damage[2] (in %) to rice |
|---|---|---|---|
| (A1.1)[S] | 45 | 0 | 0 |
| (B1.11) | 3000 | 83 | 5 |
| (A1.1)[S] + (B1.11) | 45 + 3000 | 96 (E = 83) | .3 |

TABLE 8

Herbicidal effect and selectivity in rice (field trial)

| Active compound(s) | Dose[1] g of AS/ha | Herbicidal effect[2] (in %) against IPOHE | Damage[2] (in %) to rice |
|---|---|---|---|
| (A1.1)[S] | 45 | 0 | 1 |
| (B4.25) | 30 | 78 | 0 |
| (A1.1)[S] + (B4.25) | 45 + 30 | 90 (E = 78) | .0 |

TABLE 9

Herbicidal effect and selectivity in rice (field trial)

| Active compound(s) | Dose[1] g of AS/ha | Herbicidal effect[2] (in %) against AMARE | Damage[2] (in %) to rice |
|---|---|---|---|
| (A1.1)[S] | 60 | 0 | 4 |
| (B3.1) | 50 | 66 | 18 |
| (A1.1)[S] + (B3.1) | 60 + 50 | 100 (E = 96) | .20 |

TABLE 10

Herbicidal effect and selectivity in rice (field trial)

| Active compound(s) | Dose[1] g of AS/ha | Herbicidal effect[2] (in %) against SEBEX | Damage[2] (in %) to rice |
|---|---|---|---|
| (A1.1)[S] | 75 | 0 | 4 |
| (B2.2) | 32 | 93 | 13 |
| (A1.1)[S] + (B2.2) | 75 + 32 | 100 (E = 93) | .13 |

Abbreviations for Tables 7, 8, 9 and 10:
[1] = application in each case post-emergence at the 2-4-leaf stage,
[2] = scoring 28 days after application
(A1.1)[S] = fenoxaprop-P-ethyl in combination with the safener (S1-9)
(S1-9) = ethyl 5,5-diphenyl-2-isoxazoline carboxylate
(61.11) = benthiocarb (thiobencarb)
(64.25) = pyribenzoxim
(B3.1) = triclopyr
(B2.2) = carfentrazone
ECHCG = Echinochloa crus-galli
IPOHE = Ipomea hederaceae
AMARE = Amaranthus retroflexus
SEBEX = Sebania exaltata

TABLE 11

Herbicidal effect and selectivity in rice (field trial)

| Active compound(s) | Dose[1] g of AS/ha | Herbicidal effect[2] (in %) against CYPDI | Herbicidal effect[2] (in %) against IPOSS | Damage[2] (in %) to rice |
|---|---|---|---|---|
| (A1.1)[S] | 45 | 0 | 0 | 27 |
| (B4.6) | 45 | 75 | 91 | 16 |
| (A1.1)[S] + (B4.6) | 45 + 45 | 89 (E = 75) | 95 (E = 91) | .31 |

Abbreviations for Table 11:
[1] = application in each case post-emergence at the 2-4-leaf stage,
[2] = scoring 28 days after application
(A1.1)[S] = fenoxaprop-P-ethyl in combination with the safener (S1-9)
(S1-9) = ethyl 5,5-diphenyl-2-isoxazoline carboxylate
(B4.6) = bispyribac-Na
CYPDI = Cyperus difformis
IPOSS = Ipomoea spp

TABLE 12

Herbicidal effect and selectivity in rice (field trial)

| Active compound(s) | Dose[1] g of AS/ha | Herbicidal effect[2] (in %) against ECHCG | Damage[2] (in %) to rice |
|---|---|---|---|
| (A1.1) | 80 | 97 | 5 |
|  | 40 | 95 | 0 |
|  | 20 | 80 | 0 |
| (B1.7) | 5000 | 30 | 5 |
|  | 2500 | 10 | 5 |
|  | 1250 | 0 | 0 |
| (A1.1) + (B1.7) | 20 + 1250 | 93 (E = 80) | 0 |
|  | 20 + 2500 | 98 (E = 90) | 3 |

Abbreviations for Table 12:
[1] = application in each case post-emergence at the 3-leaf stage,
[2] = scoring 12 days after application
(A1.1) = fenoxaprop-P-ethyl
(B1.7) = propanil
ECHCG = Echinochloa crus-galli

TABLE 13

Herbicidal effect and selectivity in rice (field trial)

| Active compound(s) | Dose[1] g of AS/ha | Herbicidal effect[2] (in %) against ECHCG | Damage[2] (in %) to rice |
|---|---|---|---|
| (A1.1)[S] | 20 | 75 | 0 |
| (B2.4) | 37.5 | 0 | 0 |
| (A1.1)[S] + (B2.4) | 20 + 37.5 | 85 (E = 75) | 0 |

Abbreviations for Table 13:
[1] = application in each case post-emergence at the 1-2-leaf stage,
[2] = scoring 28 days after application
(A1.1)[S] = fenoxaprop-P-ethyl in combination with the safener (S1-9),
(S1-9) = ethyl 5,5-diphenyl-2-isoxazoline carboxylate
(B2.4) = tritosulfuron
ECHCG = *Echinochloa crus-galli*

TABLE 14

Herbicidal effect and selectivity in rice (field trial)

| Active compound(s) | Dose[1] g of AS/ha | Herbicidal effect[2] (in %) against CYPIR | Damage[2] (in %) to rice |
|---|---|---|---|
| (A1.1)[S] | 60 | 0 | 0 |
|  | 75 | 0 | 0 |
| (B4.2) | 300 | 30 | 0 |
| (A1.1)[S] + (B4.2) | 75 + 300 | 50 (E = 30) | 0 |
| (B4.8) | 250 | 75 | 0 |
| (A1.1)[S] + (B4.8) | 75 + 250 | 82 (E = 75) | 0 |
| (B1.11) | 1500 | 78 | 0 |
| (A1.1)[S] + (B1.11) | 75 + 1500 | 82 (E = 78) | 0 |

Abbreviations for Table 14:
[1] = application in each case post-emergence at the 3-leaf stage,
[2] = scoring 42 days after application
(A1.1)[S] = fenoxaprop-P-ethyl in combination with the safener (S1-9),
(S1-9) = ethyl 5,5-diphenyl-2-isoxazoline carboxylate
(B4.2) = clomazone
(B4.8) = oxadiazon
(B1.11) = thiobencarb
CYPIR = *Cyperus iria*

The invention claimed is:

1. A herbicide-combination comprising:
a herbicidally effective content of a synergistic combination of (A) fenoxaprop-P-ethyl and (B) propanil;
wherein the ratio by weight of (A):(B) is 1:200 to 5:2.

2. A method for controlling harmful plants in rice crops, which comprises:
applying a synergistic combination of (A) fenoxaprop-P-ethyl and (B) propanil in rice crops;
wherein the ratio by weight of (A):(B) is 1:200 to 5:2.

3. The method according to claims 2;
wherein (A) 5 to 500 g a.i./ha fenoxaprop-P-ethyl and (B) 10 to 4000 g a.i./ha propanil are applied.

* * * * *